US012799155B2

(12) United States Patent
Lenna et al.

(10) Patent No.: US 12,799,155 B2
(45) **Date of Patent: *Nov. 17, 2026**

(54) PROCESS FOR THE PREPARATION OF B-[(7ALPHA, 17BETA)-17-HYDROXY-7-[9-[(4,4,5,5,5-PENTAFLUOROPENTYL) SULFINYL]NONYL]ESTRA-1,3,5(10)-TRIEN-3-YL]-BORONIC ACID AND INTERMEDIATES OF SAID PROCESS

(71) Applicant: INDUSTRIALE CHIMICA S.R.L., Milan (IT)

(72) Inventors: Roberto Lenna, S. Giorgio Su Legnano (IT); Andrea Fasana, Nesso (IT)

(73) Assignee: Industriale Chimica S.R.L., Milan (IT)

( * ) Notice: Subject to any disclaimer, the term of this patent is extended or adjusted under 35 U.S.C. 154(b) by 516 days.

This patent is subject to a terminal disclaimer.

(21) Appl. No.: 18/288,930

(22) PCT Filed: Oct. 29, 2021

(86) PCT No.: PCT/IB2021/060015

§ 371 (c)(1),
(2) Date: Oct. 30, 2023

(87) PCT Pub. No.: WO2022/238752

PCT Pub. Date: Nov. 17, 2022

(65) Prior Publication Data

US 2024/0218013 A1 Jul. 4, 2024

(30) Foreign Application Priority Data

May 11, 2021 (IT) ........................ 102021000012062

(51) Int. Cl.
*C07J 51/00* (2006.01)
*C07J 31/00* (2006.01)

(52) U.S. Cl.
CPC ............. *C07J 51/00* (2013.01); *C07J 31/006* (2013.01)

(58) Field of Classification Search
CPC ................................ C07J 51/00; C07J 31/006
See application file for complete search history.

(56) References Cited

U.S. PATENT DOCUMENTS 12,600,745 B2 * 4/2026 Lenna .................... C07J 31/006

FOREIGN PATENT DOCUMENTS

WO 95/000478 1/1995
WO 2016004166 1/2016
WO 2020187658 9/2020

OTHER PUBLICATIONS

International Search Report and Written Opinion for International Application No. PCT/IB2021/060015, dated Feb. 24, 2022, 15 pages.

* cited by examiner

*Primary Examiner* — Rebecca L Anderson
(74) *Attorney, Agent, or Firm* — Fish IP Law, LLP

(57) ABSTRACT

The present invention relates to a process for preparing B-[(7α, 17β)-17-hydroxy-7-[9-[(4,4,5,5,5-pentafluoropentyl)sulfi nyl]estra-1,3,5(10)-trien-3-yl]-boronic acid, known as Fulvestrant-3-boronic acid or ZB716, whose structure is reported below: Formula (I) ZB716

Formula (I)

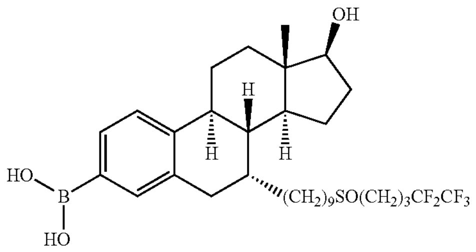

ZB716

8 Claims, No Drawings

PROCESS FOR THE PREPARATION OF B-[(7ALPHA, 17BETA)-17-HYDROXY-7-[9-[(4,4,5,5,5-PENTAFLUOROPENTYL) SULFINYL]NONYL]ESTRA-1,3,5(10)-TRIEN-3-YL]-BORONIC ACID AND INTERMEDIATES OF SAID PROCESS

FIELD OF THE INVENTION

The present invention relates to the sector of processes for the synthesis of active ingredients for pharmaceutical use, and in particular to a process for preparing B-(7α, 17β)-hydroxy-7-[9-[(4,4,5,5,5-pentafluoropentyl)sulfinyl]nonyl] estra-1, 3, 5(10)-trien-3-yl]-boronic acid, also known as Fulvestrant-3-boronic acid or ZB716, on an industrial scale. The compound is identified by the CAS Number 1853279-29-4.

The invention further relates to an intermediate of said process.

STATE OF THE ART

ZB716 is useful for the treatment of metastatic breast cancer. The structure of the compound is shown below: OH

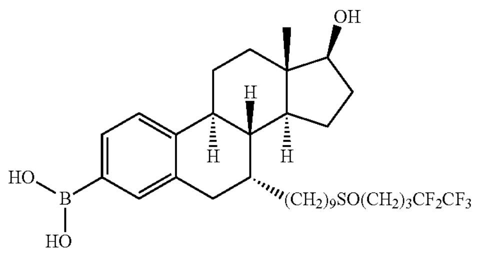

ZB716

The compound is described and claimed in EP Patent No. 3473630 B 1 (Compound 29, claim 1) by Xavier University of Louisiana.

The article "Fulvestrant-3 boronic acid (ZB716): an orally bioavailable selective estrogen receptor downregulator (SERD)", J. Liu et al., J. Med. Chem. 2016, 59, 8134-8140, reports an experimental description of the preparation of the compound in question (page 8135, Scheme 1); this synthesis starts from the compound KSM, having the formula shown below:

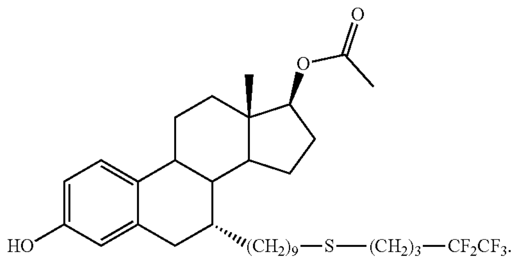

The compound KSM can in turn be obtained by following what is reported in the article "Fulvestrant: from the laboratory to commercial-scale manufacture", E. J. Brazier et al., Org. Process Res. Dev. 2010, 14, 3, 544-552, which describes the synthesis of another active ingredient, Fulvestrant, also currently used for the treatment of metastatic breast cancer.

As can be learned by reading J. Med. Chem. 2016, 59, 8134-8140, the compound ZB716 shows apparent clinical advantages over Fulvestrant that shares with it a large portion of the structure.

In the following figure the structural differences between Fulvestrant and ZB716 are highlighted:

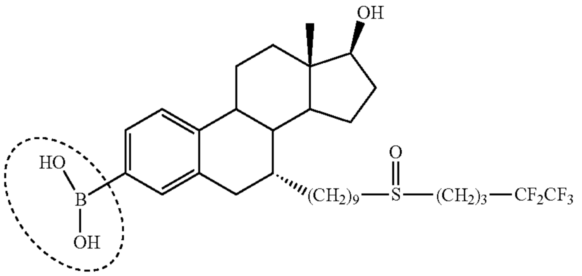

ZB716

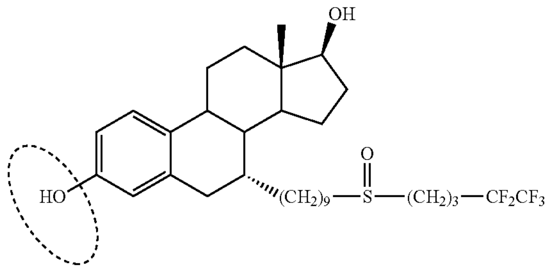

FULVESTRANT

The Applicant has been producing Fulvestrant for years but with a different process from that described in Organic Process Research & Development 2010, 14, 544-552.

This process does not involve the use of intermediate 1 by J. Med. Chem. 2016, 59, 8134-8140, having the following structural formula:

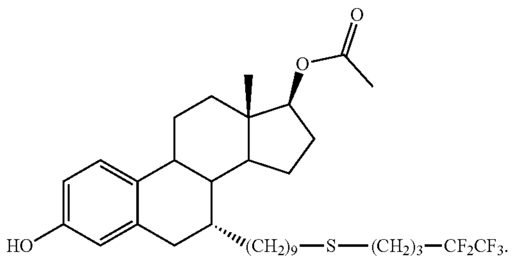

The Applicant has therefore developed a new, industrially applicable, synthetic route for ZB716 which uses Fulvestrant as starting material.

SUMMARY OF THE INVENTION

This object is achieved with the present invention, which in a first aspect relates to a process for the synthesis of ZB716 and comprises the following steps:

a) reaction of Fulvestrant, (7α, 17β)-7-[9-[(4,4,5,5,5-pentafluoropentyl)sulfinyl]nonyl]-estra 1,3,5(10)trien-3, 17-diol, intermediate N-4 of the process, with a triflating agent, obtain intermediate N-3, (7α, 17β)-7-[9-[(4, 4,5,5,5-pentafluoropentyl)sulfinyl]nonyl]-estra-1,3,5 (10)-trien-17-ol3-triflate:

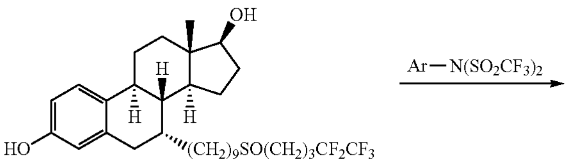

N-4

-continued

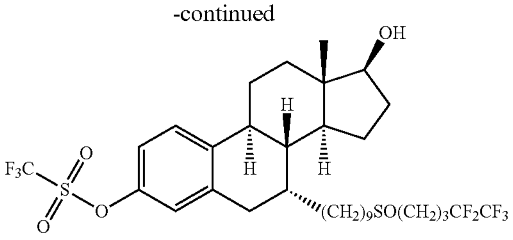

N-3 b) reaction of intermediate N-3 with 4,4,4',4',5,5,5',5'-octamethyl-2,2'-bi-1,3,2-dioxaborolane to obtain intermediate N-2, (7α 17β)-7-[9[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-ol:

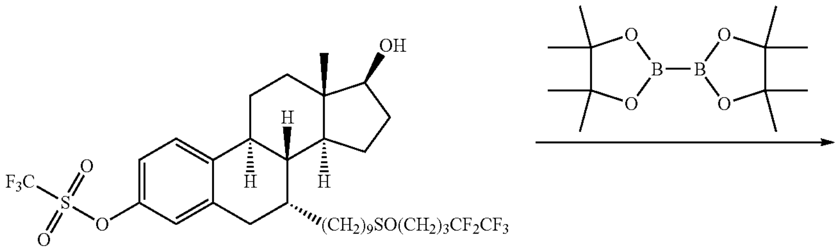

N-3

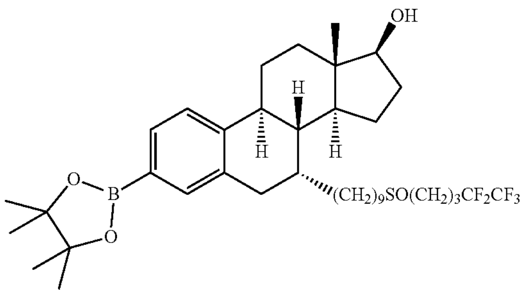

N-2 c) reaction of intermediate N-2 with $KHF_2$ to obtain intermediate N-1, potassium (7α 17β)-7-[9-[(4,4,5,5,5-pentafluoropentyl)sulfinyl]nonyl]-estra-1, 3, 5(10)-trien-17-ol-3-trifluoroborate:

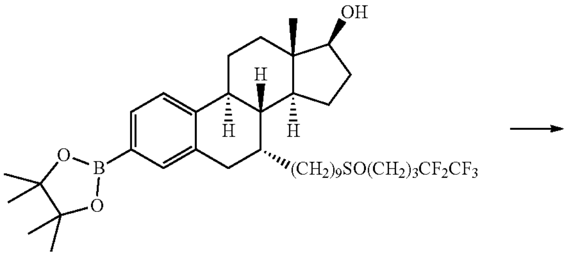

N-2

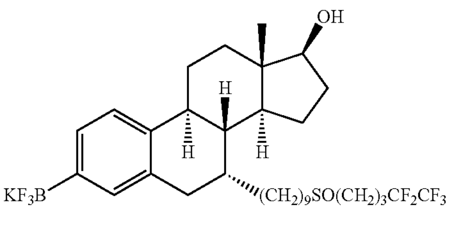

N-1 d) treatment of intermediate N-1 to give compound ZB716,B[(7α, 17β)-17-hydroxy-7-[9-[(4,4,5,5,5-pentafluoropentyl)sulfinyl]nonyl]estra-1, 3, 5(10)-trien-3-yl]-boronic acid:

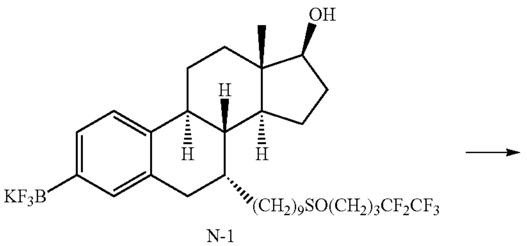

N-1

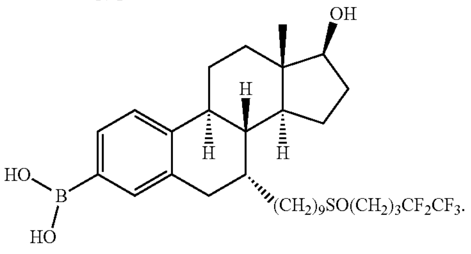

ZB716

In its second aspect, the invention relates to the compounds:

7α, 17β)-7-[9-[(4,4,5,5,5-pentafluoropentyl)sulfinyl]nonyl]-estra-1,3,5(1(10)-trien-17-ol 3-triflate:

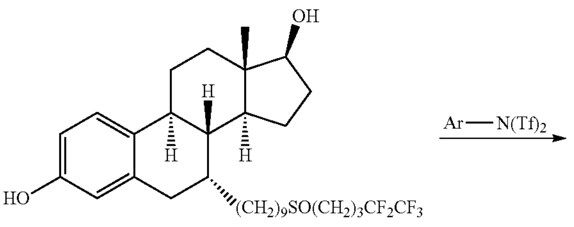

N-4

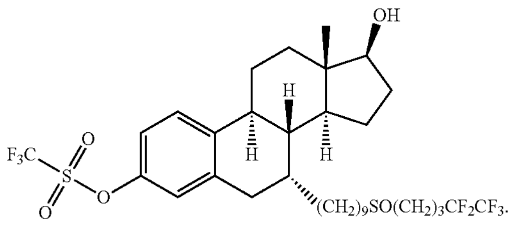

N-3 and potassium (7α, 17β)-7-[9-[(4,4,5,5,5-pentafluoropentyl)sulfinyl]nonyl]-estra-1, 3, 5(10)-trien-17-ol-3-trifluoroborate:

N-3

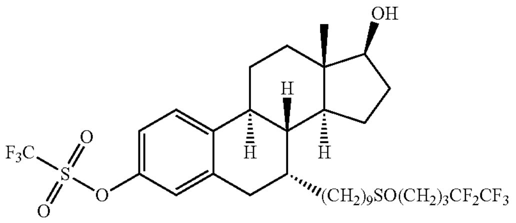

DETAILED DESCRIPTION OF THE INVENTION

In its first aspect, the invention relates to a process for the synthesis of ZB716 comprising the steps described below.

In the description of the reactions forming the process of the invention, the ratios between reagents are indicated as w/w, i.e. ratios by weight, unless otherwise specified.

Step a) consists in the reaction of Fulvestrant, (7α, 17β)-7-[9-[(4,4,5,5,5-pentafluoropentyl)sulfinyl]nonyl]-estra-7, 5(10)-triers-3,17-dial, intermediate N-4 of the process, with a triflating agent, to obtain intermediate N-3, (7α, 17β)-7-[9 [(4,4,5,5,5-pentafluoropentyl)sulfinyl]nonyl]-estra-1, 3, 5(10)-trien-3,17-diol 3-triflate:

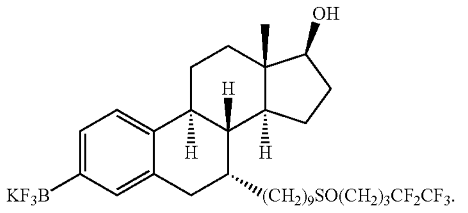

Fulvestrant, of a quality suitable for use in the process of the present invention, can be obtained either by following the process described in EP 2183267, or using commercially available Fulvestrant.

Triflation exclusively occurs at the phenolic hydroxy group without having to protect the other hydroxy group present in the molecule using an aromatic bis(trifluoromethanesulfonimide) of general formula Ar—N(Tf)$_2$ as triflating agent, wherein Ar indicates the aromatic or heteroaromaytic radical and the N(Tf)$_2$ group is the radical:

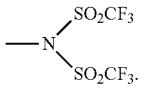

For the purposes of the present invention, the preferred triflating agent is the compound 1,1,1-trifluoro-N-phenyl-N-[(trifluoromethyl)sulfonyl]methanesulfonamide (also commonly referred to as N,N-bis(trifluoromethanesulfonyl) aniline), having the formula shown below:

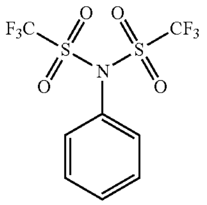 [SMILES: O=S(=O)(N(c1ccccc1)S(=O)(=O)C(F)(F)F)C(F)(F)F]

The triflating agent is used in a (w/w) ratio comprised between 0.30 and 1.20 with respect to intermediate N-4, preferably it is used in a (w/w) ratio between 0.6 and 0.9.

The reaction is carried out in dichloromethane (DCM), operating at a temperature comprised between −15 and 40° C., preferably between 0 and 30° C., for a time comprised between 4 and 12 hours, preferably between 6 and 8 hours, in the presence of an organic base selected from triethylamine, diisopropylethylamine, pyridine, 4-(dimethylamino) pyridine, 2,6-lutidine. Triethylamine is preferably used.

Step b) consists in the reaction of intermediate N-3 with 4,4,4',4',5,5,5',5'-octamethyl-2,2'-bi-1,3,2-dioxaborolane to obtain intermediate N-2, (7α, 17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-ol,

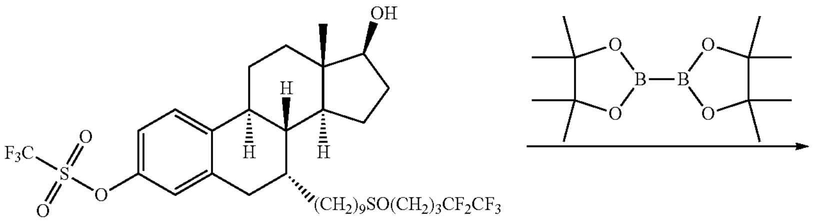

N-3

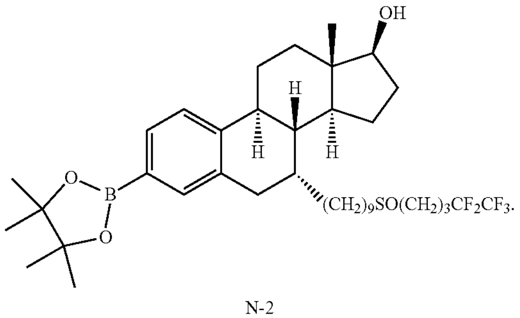

N-2

The compound 4,4,4',4',5,5,5',5'-octamethyl-2,2'-bi-1,3,2-dioxaborolane is commercially available and is also referred to by the common name of bis(pinacolato)diboron.

Bis(pinacolato)diboron is used in a (w/w) ratio comprised between 0.20 and 0.45, preferably between 0.25 and 0.40, with respect to intermediate N-3.

The reaction is carried out in acetonitrile operating at a temperature comprised between 70 and 90° C., preferably between 35 and 75° C., for a time comprised between 1 and 6 hours, preferably between 2 and 5 hours, in the presence of an organic derivative of palladium(II) such as palladium (II) acetate, a phosphine such as tricyclohexylphosphine, and a base such as sodium or potassium acetate or sodium or potassium methylate; the preferred bases are potassium acetate and potassium methylate.

Step c) consists in the reaction of intermediate N-2 with $KHF_2$ to obtain intermediate N-1, potassium (7α, 17β)-7-[9-[(4,4,5,5,5-pentafluoropentyl)sulfinyl]nonyl]-estra-1, 3, 5(10)-trien-17-ol-3-trifluoroborate:

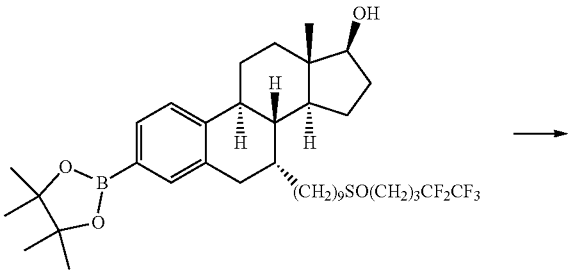

N-2

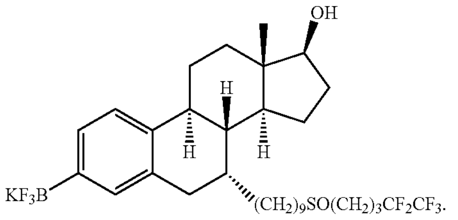

N-1

The compound potassium hydrogen difluoride, $KHF_2$, is commercially available and is also referred to by the common name of potassium bifluoride.

Its use is also known, as reported in Chem. Rev, 2008, 108, pages 288-325, for the preparation of potassium organofluoroborates.

Specifically, for the conversion from pinacolborate to trifluoroborate see Tetrahedron Letters 2005, vol 46, pages 7899-7903, which exemplifies the reaction on an optionally substituted phenyl, according to the following general scheme (the reaction occurs at room temperature):

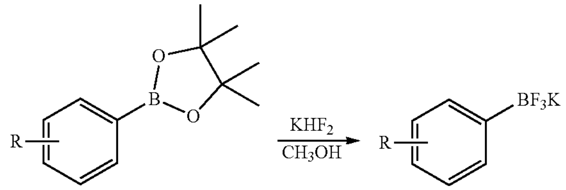

Potassium bifluoride, $KHF_2$, is used in a (w/w) ratio comprised between 0.45 and 0.75, preferably between 0.55 and 0.70, with respect to intermediate N-2.

The reaction is carried out in an alcohol such as ethanol, methanol, isopropanol, tert-butanol or in acetone, THE or a mixture of acetonitrile and water, operating at a temperature comprised between 10 and 40° C., preferably between 15 and 35° C., for a time comprised between 30 minutes and 4 hours, preferably between 45 minutes and 2 hours.

Finally, in step d) of the process, intermediate N-1 is reacted to give compound ZB716, B-[(7α, 17β)-17-hydroxy-7-[9-[(4,4,5,5,5-pentafluoropentyl)sulfinyl]nonyl]estra-1, 3, 5(10)-trien-3-yl]-boronic acid:

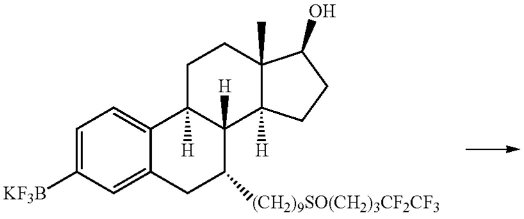

N-1

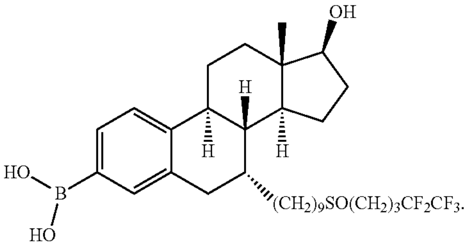

ZB716

Alkali metal hydroxides, silicon compounds, carbonates (lithium, sodium or potassium carbonate), or bicarbonates (of sodium and potassium) can be used as reagents.

When using hydroxides, lithium hydroxide hydrate, potassium hydroxide and sodium hydroxide can be used.

Lithium hydroxide monohydrate is preferably used.

When using lithium hydroxide monohydrate, the reagent is used in a (w/w) ratio comprised between 0.1 and 1.5, preferably between 0.15 and 1.0, with respect to intermediate N-1.

The reaction is carried out using as solvent a mixture of water with a water miscible solvent, such as methanol, tetrahydrofuran (THF) or acetone.

Preferred reaction conditions are the use of aqueous acetonitrile, a temperature comprised between 10 and 45° C., preferably between 20 and 30° C., and a reaction time comprised between 8 hours and 36 hours, preferably between 16 and 30 hours.

When using silicon compounds, trimethylsilyl chloride, triethylsilyl chloride, dimethylethylsilyl chloride or tert-butyldimethylsilyl chloride can be used. Preferably trimethylsilyl chloride is used.

When using trimethylsilyl chloride, the reagent is used in a (w/w) ratio comprised between 0.3 and 0.7, preferably between 0.4 and 0.6, with respect to intermediate N-1.

The reaction is carried out using as solvent a mixture of water with a solvent miscible with water, such as methanol, tetrahydrofuran (THF), acetonitrile or acetone.

Preferred reaction conditions are the use of aqueous acetonitrile, a temperature comprised between 10 and 45° C., preferably between 20 and 30° C., and a reaction time comprised between 30 minutes and 3 hours, preferably between 45 minutes and 2 hours.

In its second aspect, the invention relates to the compounds:

(7a 17β)-7-[9-[(4,4,5,5,5-pentafluoropentyl)sulfinyl]nonyl]-estra-1, 3, 5(10)-trien-17-ol-3-triflate:

N-3

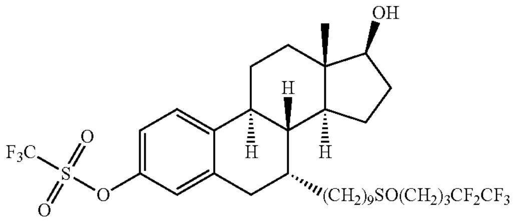

and potassium (7α, 17β)-7-[9-[(4,4,5,5,5-pentafluoropentyl)sulfinyl]nonyl]-estra-1, 3, 5(10)-trien-17-ol-3-trifluoroborate:

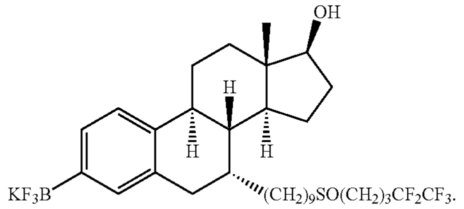

The invention will be further illustrated by the following examples.

Instruments, Methods and Experimental Conditions

NMR:

NMR spectrometer JEOL 400 YH (400 MHz); Software JEOL Delta v5.1.1;

Spectra recorded in deuterated solvents such as: Chloroform-d, D 99.8%, containing 0.1% (v/v) tetramethylsilane (TMS) as internal standard; and Chloroform-d, "100%", D99.96%, containing 0.03% (v/v) TMS, and DMSO-$d_6$.

MS 1:

Instrument: DSQ-trace Thermofisher

Sample introduction—direct exposure probe (dep)

Chemical ionization (CI) with methane

Methane pressure: 2.2 psi

Source Temperature: 200° C.

MS 2:

Instrument: Waters Acquity UPLC QDa Detector

Electrospray ionization (ESI) with formic acid

Source Temperature: 120° C.

UPLC:

Chromatographic System: Waters Acquity UPLC; Detector: Acquity UPLC PDA and X Detector Chromatographic Conditions:

Column: Acquity UPLC BEH C18 1.7 μm, 2.1×50 mm

Flow Rate: 0.5 mL/min

Detector: UV 225 nm

Injection Volume: 1 μL

Temperature: 35° C.

Mobile phase A: $H_2O$+0.01% formic acid (FA)

Mobile phase B: Acetonitrile+0.01% formic acid (FA)

| TIME (MIN.) | MOBILE PHASE A (V/V) | MOBILE PHASE B (V/V) |
|---|---|---|
| 0.00 | 70 | 30 |
| 0.00-1.00 | 70 | 30 |
| 1.00-5.00 | 10 | 90 |
| 5.00-6.00 | 10 | 90 |
| 6.00-9.50 | 0 | 100 |
| 9.50-9.60 | 70 | 30 |
| 9.60-10.50 | 70 | 30 |

TLC

MERCK: TLC silica gel 60 $F_{254}$ Aluminium sheets 20×20 cm, cod. 1.0554.0001.

TLC Stains

Cerium phosphomolybdate: 25 g of phosphomolybdic acid and 10 g cerium (IV) sulfate are dissolved in 600 mL of $H_2O$. 60 mL of 98% $H_2SO_4$ are added and brought to 1 L with $H_2O$. The plate is impregnated with the solution and then heated until the products are detected.

Notes

The water used in the experimental descriptions is to be intended as pure water, unless otherwise indicated.

The organic solvents used in the experimental descriptions are to be intended of "technical" grade, unless otherwise indicated.

The reagents and catalysts used in the experimental descriptions are to be intended of commercial quality, unless otherwise indicated.

Example 1

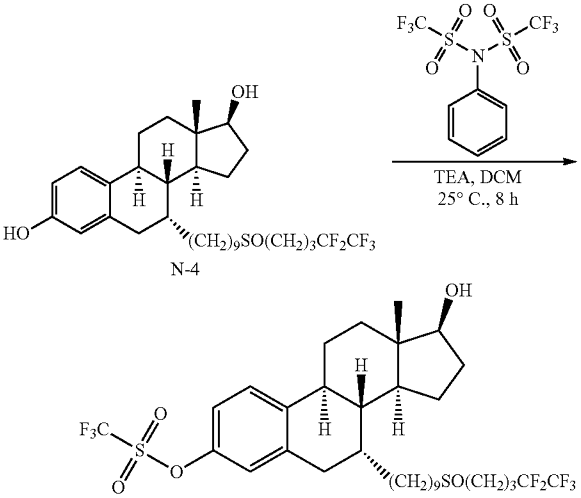

N-4 → N-3

A flask is charged with 46.8 g of Fulvestrant, 468 mL of dichloromethane and 32 mL of triethylamine (TEA).

The mixture is cooled to 5° C., and a solution of N,N-bis(trifluoromethanesulfonyl)aniline (41.3 g) dissolved in 164 mL of dichloromethane is added dropwise in about 15 minutes. The mixture is brought to 25° C. and kept under stirring for 8 hours.

Once the reaction is complete (UPLC monitoring), the solvent is removed by distilling under reduced pressure at 45° C. to obtain 99 g of Fulvestrant triflate (oil) which is reacted as such in the subsequent reaction.

The Fulvestrant used as the starting reagent of the method, subjected to $^1$H-NMR and Ms analysis, shows the following analytical data: $^{1}H$-NMR (400 MHz, DMSO-$d_6$): 8.99 (s, 1H); 7.04 (d, 1H, J=8.4 Hz); 6.49 (d, 1H, J=8.0 Hz); 6.41 (s, 1H); 4.50 (s, 1H); 3.54-3.52 (m, 1H); 2.76-0.71 (m, 38H); 0.66 (s, 3H).

The $^{1}H$-NMR signals at 8.99 ppm and 4.50 ppm (attributable to the mobile protons in position 3 and 17) disappear after deuteration of the sample with $D_2O$.

Mass (ESI): m/z=629 [$M^+$+1+22]; 607 [$M^+$+1]; 589 [$M^+$+1-$H_2O$].

The Fulvestrant triflate obtained, subjected to $^{1}H$-NMR and Ms analysis, shows the following analytical data: $^{1}H$-NMR (400 MHz, DMSO-$d_6$): disappearance of Fulvestrant signal at 8.99 (s, 1H) but not of the signal at 4.50 (s, 1H) ppm (of Fulvestrant).

Mass ($ESI^+$): m/z=761 [$M^+$+1+22]; 739 [$M^+$+1]; 619 [$M^+$+1-$HCF_2CF_3$].

Example 2

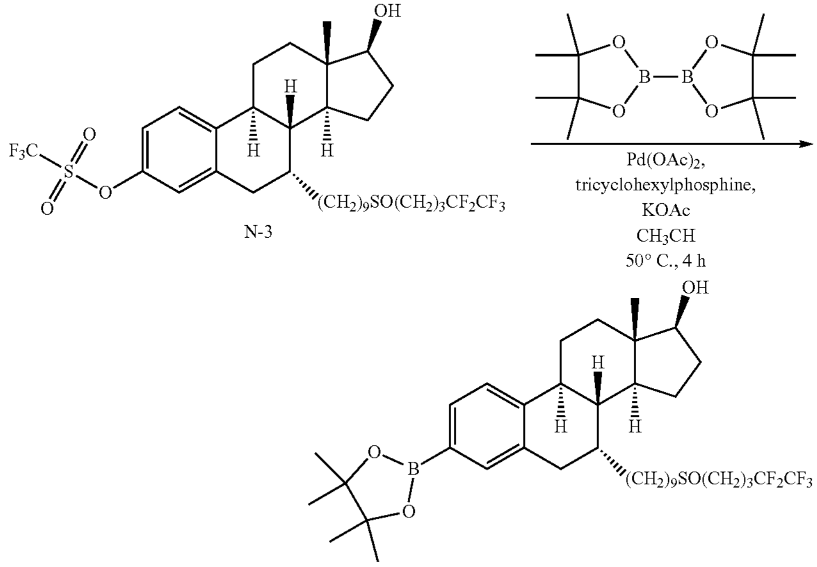

N-2

A flask is charged with the intermediate Fulvestrant triflate obtained according to the procedure described in the previous example, and 1140 mL of acetonitrile. The mixture is kept under stirring at 25° C. for 10 minutes. 29.3 g of bis(pinacolato)diboron, 20.7 g of potassium acetate, 4.6 g of tricyclohexylphosphine and 2.3 g of palladium acetate are added to the solution. The mixture is heated to 50° C. for 4 hours.

Once the reaction is complete (UPLC monitoring), the solvent is removed by distilling under reduced pressure at 45° C. to obtain 99 g of crude Fulvestrant 3-pinacolborate.

The product is purified by chromatographic column on silica gel, eluting with methylene chloride and then with a 70:30 methylene chloride/acetonitrile mixture. The solvent is concentrated under reduced pressure at 45° C. obtaining 40 g of Fulvestrant 3-pinacolborate (oil).

The intermediate Fulvestrant 3-pinacolborate is analysed by H-NMR and mass spectroscopy.

$^{1}H$-NMR (400 MHz, DMSO-$d_6$): 7.40 (d, 1H, J=7.2 Hz); 7.36 (s, 1H); 7.28 (d, 1H, J=7.2 Hz); 4.53 (d, 1H, J=4.4 Hz); 3.56-3.55 (m, 1H); 2.81-0.71 (m, 50H); 0.67 (s, 3H).

The $^{1}H$-NMR signal at 4.4 ppm disappears after deuteration of the sample with $D_2O$.

Mass (CI): m/z=745 [$M^+$+1+28]; 717 [$M^+$+1]; 699 [$M^+$+1-$H_2O$]; 591 [$M^+$+1-$B(OC(CH_3)_2)_2$]; 573 [$M^+$+1-$B(OC(CH_3)_2)_2$-$H_2O$].

Example 3

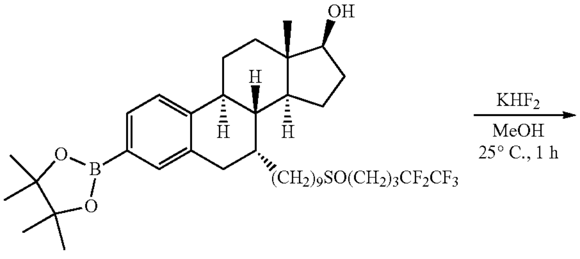

N-2

-continued

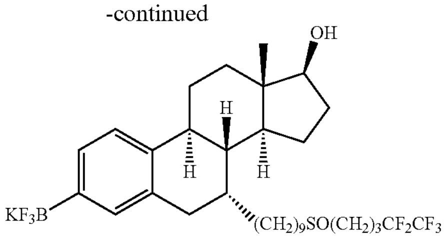

N-1

A flask is charged with Fulvestrant 3-pinacolborate (4 g) obtained according to the procedure described in the previous example and 16 mL of methanol.

A solution of potassium bifluoride (2.5 g) dissolved in water (7 mL) is added to the mixture and it is kept under stirring at 25° C. for 1 hour (the reaction is monitored by UPLC analysis).

Once the reaction is complete, the solvent is concentrated under reduced pressure at 45° C. and the residue is taken up with 30 mL of acetone. The inorganic salts present are filtered, and the filtration liquid is concentrated under reduced pressure at 45° C. obtaining 4.5 g of crude potassium Fulvestrant 3-trifluoroborate (yellow solid). The solid is taken up with 90 mL of ethyl ether and the suspension is kept under stirring at 25° C. for 1 hour. The solid is filtered washing with 45 mL of ethyl ether. The solid is resuspended with ethyl ether (90 mL), the suspension is kept under stirring at 25° C. for 1 hour and the solid is filtered washing with 45 mL of ethyl ether. The solid is dried under reduced pressure at 45° C. obtaining 3.5 g of white solid. The intermediate potassium Fulvestrant 3-trifluroborate is analysed by $^{1}$H-NMR and mass spectroscopy.

$^{1}$H-NMR (400 MHz, DMSO-$d_6$): 7.03 (d, 1H, J=8.0 Hz); 6.98 (d, 1H, J=9.1 Hz); 6.97 (s, 1H); 4.51 (d, 1H, J=4.8 Hz); 3.55-3.51 (m, 1H); 2.81-0.71 (m, 38H); 0.67 (s, 3H).

The $^{1}$H-NMR signal at 4.51 ppm disappears after deuteration of the sample with $D_2O$.

$^{19}$F-NMR (400 MHz, DMSO-$d_6$): −84.5 (s, $CF_3$); −117.1 (s, $CF_2$); −138.52 (s, $BF_3$). Mass (ESI$^-$): m/z=657.

Example 4

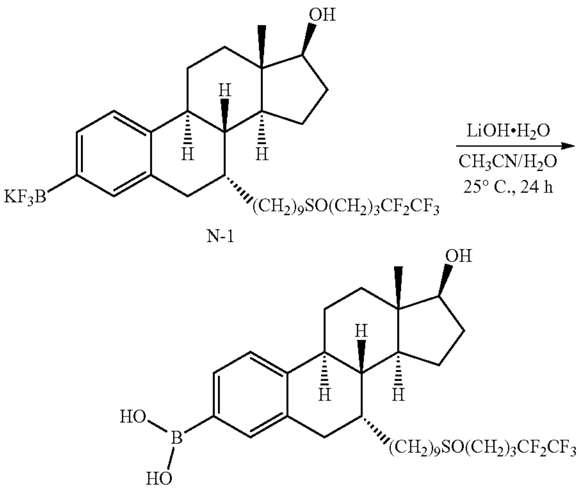

ZB716

A flask is charged with 2.5 g of potassium Fulvestrant 3-trifluoroborate and 0.53 g of lithium hydroxide monohydrate. 36 mL of acetonitrile and 18 mL of water are added.

The suspension is kept under stirring at 25° C. for 24 hours (the reaction is monitored by $^{1}$H-NMR analysis).

Once the reaction is complete, a saturated ammonium chloride solution (30 mL) and 1M hydrochloric acid (6 mL) are added. Ethyl acetate (30 mL) is added, the layers are separated, and the organic layer is re-extracted with ethyl acetate.

The organic layer is washed with a saturated sodium chloride aqueous solution and concentrated under reduced pressure at 45° C. to obtain 2.2 g of crude ZB716 (yellow solid).

The crude product is dissolved in the smallest amount of methanol and crystallized with acetonitrile.

The solid is dried under reduced pressure at 45° C. obtaining 1.1 g of the desired compound, ZB716, as a white solid, whose $^{1}$H-NMR, $^{13}$C-NMR e Ms analytical data coincide with those reported in the literature.

$^{1}$H-NMR (400 MHz, DMSO-$d_6$): 7.68 (s, 2H); 7.50 (d, 1H, J=7.6 Hz); 7.43 (s, 1H); 7.23 (d, 1H, J=7.6 Hz); 4.36 (d, 1H, J=4.4 Hz); 3.56-3.55 (m, 1H); 2.84-2.60 (m, 6H); 2.45-2.25 (m, 4H); 1.94-1.10 (m, 26H); 0.88 (m, 2H); 0.67 (s, 3H).

The $^{1}$H-NMR signals at 7.68 ppm and 4.36 ppm disappear after deuteration of the sample with $D_2O$.

$^{13}$C-NMR (400 MHz, DMSO-$d_6$): 141.8; 136.4; 134.2; 131.9; 125.3; 80.6; 51.7; 49.9; 46.7; 43.5; 42.1; 39.1; 37.4; 34.7; 33.3; 30.4; 29.8; 29.5; 29.3; 29.1; 29.0; 28.6; 28.0; 27.3; 25.6; 22.8; 22.5; 14.6; 11.8.

Mass (ESI$^+$): m/z=657 [$M^+$+1+22]; 635 [$M^+$+1]; 617 [$M^+$+1-$H_2O$].

Example 5

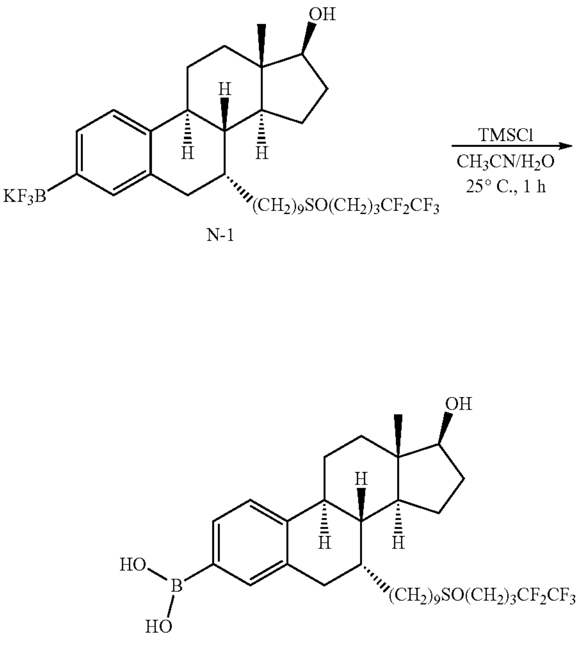

ZB716

A flask is charged with 0.5 g of potassium Fulvestrant 3-trifluoroborate, 7.5 mL of acetonitrile and water (0.05 mL).

Trimethylchlorosilane (0.3 mL) is added and the mixture is kept under stirring at 25° C. for 1 hour (the reaction is monitored by $^{1}$H-NMR analysis).

Once the reaction is complete, a saturated sodium bicarbonate solution (1.1 mL) is added, and the solution is dried with sodium sulfate. It is filtered and concentrated under reduced pressure at 45° C. obtaining 0.4 g of crude ZB716 (green solid) whose $^{1}$H-NMR, $^{13}$C-NMR and Ms analytical data coincide with those reported in the previous example.

What is claimed is:

1. A process for the synthesis of B-[(7α,17β)-17-hydroxy-7-[9-[(4,4,5,5,5-pentafluoropentyl)sulfinyl]nonyl]estra-1,3,5(10)-trien-3-yl]-boronic acid (ZB716), comprising the following steps:

a) reaction of Fulvestrant, (7α,17β)-7-[9-[(4,4,5,5,5-pentafluoropentyl)sulfinyl]nonyl]-estra-1,3,5(10)-trien-3,17-diol, intermediate N-4 of the process, with a triflating agent, to obtain intermediate N-3, (7α,17β)-7-[9-[(4,4,5,5,5-pentafluoropentyl)sulfinyl]nonyl]-estra-1,3,5(10)-trien-17-ol 3-triflate:

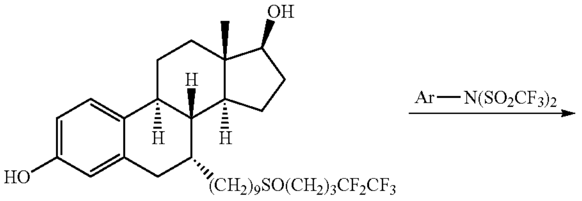

N-4

-continued

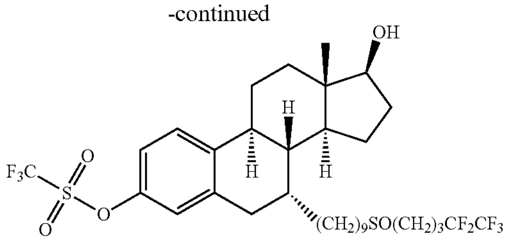

N-3 wherein Ar—$N(SO_2CF_3)_2$ is an aromatic or heteroaromatic bis(trifluoromethanesulfonimide) used as triflating agent, wherein Ar indicates the aromatic or heteroaromatic radical;

b) reaction of intermediate N-3 with 4,4,4',4',5,5,5',5'-octamethyl-2,2'-bi-1,3,2-dioxaborolane to obtain intermediate N-2, (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-ol:

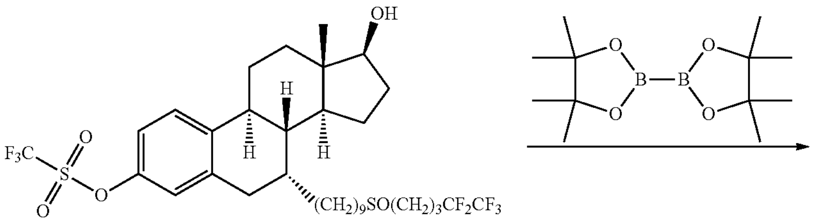

N-3

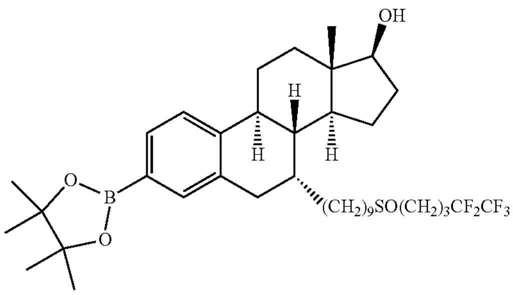

N-2 c) reaction of intermediate N-2 with $KHF_2$ to obtain intermediate N-1, potassium (7α,17β)-7-[9-[(4,4,5,5,5-pentafluoropentyl)sulfinyl]nonyl]-estra-1,3,5(10)-trien-17-ol-3-trifluoroborate:

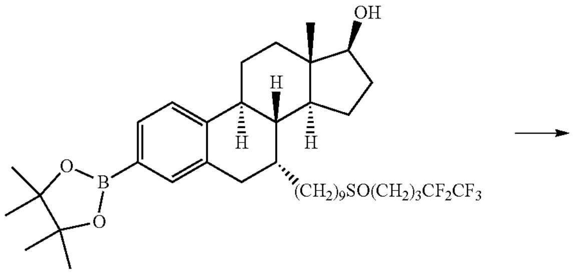

N-2

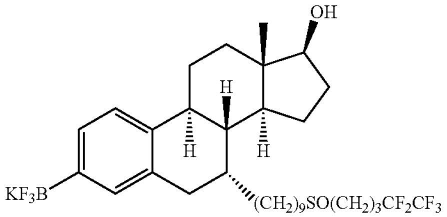

N-1 d) treatment of intermediate N-1 to give compound ZB716, B-[(7α,17ß)-17-hydroxy-7-[9-[(4,4,5,5,5-pentafluoropentyl)sulfinyl]nonyl]estra-1,3,5(10)-trien-3-yl]-boronic acid:

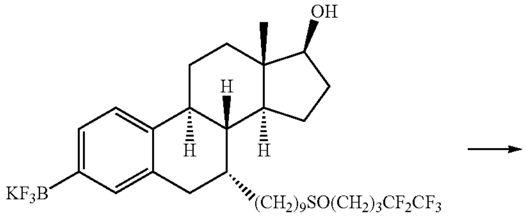

N-1

-continued

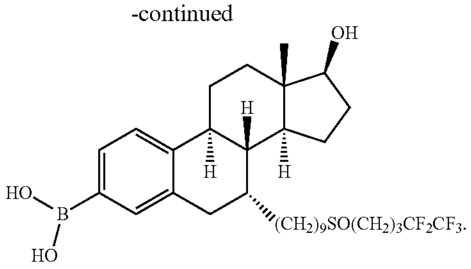

ZB716

2. The process of claim 1, wherein said triflating agent is 1,1,1-trifluoro-N-phenyl-N-[(trifluoromethyl)sulfonyl] methanesulfonamide.

3. The process of claim 1, wherein step b) is carried out in the presence of palladium (II) acetate, tricyclohexylphosphine, and a base selected from potassium acetate and potassium methylate.

4. The process of claim 1, wherein in step d) intermediate N-1 is treated with a compound which is selected from the group consisting of an alkali metal hydroxide, a silicon compound, an alkali metal carbonate, sodium bicarbonate and potassium bicarbonate.

5. The process of claim 4, wherein said alkali metal hydroxide is selected from lithium hydroxide, sodium hydroxide, potassium hydroxide and lithium hydroxide monohydrate, said silicon compound is selected from trimethylsilyl chloride, triethylsilyl chloride, dimethylethylsilyl chloride, and tert-butyldimethylsilyl chloride, and said alkali metal carbonate is selected from lithium carbonate, sodium carbonate and potassium carbonate.

6. The process of claim 4, wherein in step d) intermediate N-1 is treated with lithium hydroxide monohydrate.

7. The process of claim 4, wherein in step d) intermediate N-1 is treated with trimethylsilyl chloride.

8. A compound potassium (7α,17β)-7-[9-[(4,4,5,5,5-pentafluoropentyl)sulfinyl]nonyl]-estra-1,3,5(10)-trien-17-ol-3-trifluoroborate:

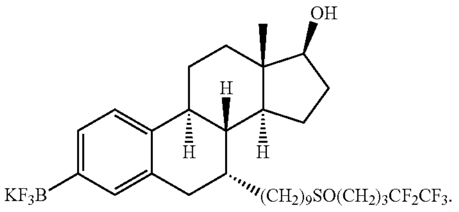

* * * * *